United States Patent
Griswold et al.

(10) Patent No.: US 11,079,448 B2
(45) Date of Patent: Aug. 3, 2021

(54) SYSTEM AND METHOD FOR PROTON DENSITY MAPPING AND RECEIVER BIAS CORRECTION USING MAGNETIC RESONANCE FINGERPRINTING (MRF)

(71) Applicant: Case Western Reserve University, Cleveland, OH (US)

(72) Inventors: Mark A. Griswold, Shaker Heights, OH (US); Anagha Deshmane, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/461,549

(22) PCT Filed: Nov. 15, 2017

(86) PCT No.: PCT/US2017/061726
§ 371 (c)(1),
(2) Date: May 16, 2019

(87) PCT Pub. No.: WO2018/093847
PCT Pub. Date: May 24, 2018

(65) Prior Publication Data
US 2019/0353718 A1   Nov. 21, 2019

Related U.S. Application Data

(60) Provisional application No. 62/422,934, filed on Nov. 16, 2016.

(51) Int. Cl.
*G01R 33/24* (2006.01)
*A61B 5/00* (2006.01)
(Continued)

(52) U.S. Cl.
CPC .......... *G01R 33/246* (2013.01); *A61B 5/0042* (2013.01); *A61B 5/055* (2013.01);
(Continued)

(58) Field of Classification Search
CPC .. G01R 33/246; G01R 33/4828; G01R 33/50; G01R 33/565; G01R 33/561; G01R 33/5659; A61B 5/0042; A61B 5/055
See application file for complete search history.

(56) References Cited

U.S. PATENT DOCUMENTS 8,643,363 B2   2/2014 Warntjes
8,723,518 B2   5/2014 Seiberlich et al.
(Continued)

FOREIGN PATENT DOCUMENTS

GB     1578910 A    11/1980

OTHER PUBLICATIONS

Gelman et al., Interregional Variation of Longitudinal Relaxation Rates in Human Brain at 3.0 T: Relation to Estimated Iron and Water Contents; Magnetic Resonance in Medicine 45: 71-79 (2001).
(Continued)

*Primary Examiner* — G. M. A Hyder
(74) *Attorney, Agent, or Firm* — Quarles & Brady LLP

(57) ABSTRACT

A system and method is provided for correcting receiver bias during quantitative proton density mapping with magnetic resonance fingerprinting (MRF). The method comprises acquiring MRF data from a region of interest in a subject by performing a pulse sequence using a series of varied sequence blocks to elicit a series of signal evolutions. The method further comprises comparing the MRF data to a MRF dictionary to simultaneously map proton density and another tissue property from the region of interest, the proton density map having a proton density signal and a receiver sensitivity profile signal. The method also includes
(Continued)

quantifying the proton density signal and the receiver sensitivity profile signal using parameters provided by the proton density map and the tissue property map, and generating a quantitative map from the region of interest based on the proton density signal.

16 Claims, 6 Drawing Sheets

(51) Int. Cl.
*A61B 5/055* (2006.01)
*G01R 33/48* (2006.01)
*G01R 33/50* (2006.01)
*G01R 33/565* (2006.01)

(52) U.S. Cl.
CPC ......... *G01R 33/4828* (2013.01); *G01R 33/50* (2013.01); *G01R 33/565* (2013.01)

(56) References Cited

U.S. PATENT DOCUMENTS

| | | | | |
|---|---|---|---|---|
| 2013/0265047 A1* | 10/2013 | Griswold | ............... | G01R 33/56 324/309 |
| 2014/0167754 A1* | 6/2014 | Jerecic | ................... | G01R 33/56 324/309 |
| 2015/0301141 A1 | 10/2015 | Griswold et al. | | |
| 2015/0301142 A1* | 10/2015 | Griswold | ........... | G01R 33/4828 324/309 |
| 2015/0302579 A1* | 10/2015 | Griswold | ........... | G01R 33/5608 382/128 |
| 2015/0346300 A1* | 12/2015 | Setsompop | ........ | G01R 33/4828 324/309 |
| 2016/0282430 A1* | 9/2016 | Gulani | ............... | G01R 33/4828 |
| 2018/0217220 A1* | 8/2018 | Gulani | ................... | G01R 33/50 |

OTHER PUBLICATIONS

Fatouros et al., Use of Magnetic Resonance Imaging for In Vivo Measurements of Water Content in Human Brain: Method and Normal Values; J. Neurosurg 90: 109-115 (1999).

Fatouros et al., In Vivo Brain Water Determination by T[sub-1] Measurements: Effect of Total Water Content, Hydration Fraction, and Field Strength; Magnetic Resonance in Medicine 17: 402-413 (1991).

Volz et al., Quantitative Proton Density Mapping: Correcting the Receiver Sensitivity Bias via Pseudo Proton Densities; NeuroImage 63: 540-552 (2012).

International Search Report and Written Opinion for International Application PCT/US2017/061726, dated Jan. 29, 2018, 34 pages.

Ma et al., Magnetic Resonance Fingerprinting, Nature 495(7440): 187-192, Mar. 14, 2013.

European Patent Office. Extended European Search Report for application 17871451.5, dated Jun. 16, 2020.

Deshmane, A., et al. "Proton density mapping and receiver bias correction for absolute quantification with MR fingerprinting." Proceedings of the 23rd scientific meeting, International Society for Magnetic Resonance in Medicine, Honolulu. vol. 1358. 2017.

Jiang, Y., et al. "MR fingerprinting using fast imaging with steady state precession (FISP) with spiral readout." Magnetic resonance in medicine 74.6 (2015): 1621-1631.

Pierre, E. Y., et al. "Multiscale reconstruction for MR fingerprinting." Magnetic resonance in medicine 75.6 (2016): 2481-2492.

* cited by examiner

SYSTEM AND METHOD FOR PROTON DENSITY MAPPING AND RECEIVER BIAS CORRECTION USING MAGNETIC RESONANCE FINGERPRINTING (MRF)

CROSS-REFERENCE TO RELATED APPLICATIONS

This application represents the National Stage Entry of International Application PCT/US2017/061726, filed Nov. 15, 2017, which claims benefit of U.S. Provisional Patent Application 62/422,934 filed Nov. 16, 2016, both of which are hereby incorporated by reference in their entireties.

STATEMENT REGARDING FEDERALLY SPONSORED RESEARCH

This invention was made with government support under EB016728 and EB017219 awarded by the National Institutes of Health. The government has certain rights in the invention.

BACKGROUND

Conventional magnetic resonance imaging ("MRI") pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time ("TE"), while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When magnetic resonance ("MR") images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration.

Magnetic resonance fingerprinting ("MRF") us a technology, which is described, as one example, by D. Ma, et al., in "Magnetic Resonance Fingerprinting," *Nature*, 2013; 495 (7440):187-192, that allows one to characterize tissue species using nuclear magnetic resonance ("NMR"). MRF can identify different properties of a resonant species (e.g., T1 spin-lattice relaxation, T2 spin-spin relaxation, proton density) to thereby correlate this information to quantitatively assess tissue. Other properties like tissue types and superposition of attributes can also be identified using MRF. These properties and others may be identified simultaneously using MRF.

In particular, unlike conventional MRI, MRF employs a series of varied sequence blocks that simultaneously produce different signal evolutions in different resonant species (e.g., tissues) to which the radio frequency ("RF") is applied. The signals from different resonant tissues will, however, be different and can be distinguished using MRF techniques. The different signals can be collected over a period of time to identify a signal evolution for the volume. Resonant species in the volume can then be characterized by comparing the signal evolution to known evolutions. Characterizing the resonant species may include identifying a material, and tissue type. Alternatively, characterizing the resonant species may include identifying MR parameters associated with the resonant species. The "known" evolutions may be, for example, simulated evolutions calculated from physical principles and/or previously acquired evolutions. A large set of known evolutions may be stored in a dictionary.

SUMMARY OF THE DISCLOSURE

The present disclosure provides systems and methods for correcting receiver bias and quantitative proton density magnetic resonance fingerprinting (MRF). The quantitative proton density signals may be combined with tissue fraction maps to determine, for example, absolute tissue fraction maps from a region of interest.

In accordance with one aspect of the present disclosure, a method is provided for correcting receiver bias during quantitative proton density mapping with magnetic resonance fingerprinting. The method includes acquiring MRF data from a region of interest in a subject by performing a pulse sequence using a series of varied sequence blocks to elicit a series of signal evolutions. The MRF data is then compared to a MRF dictionary to simultaneously map proton density and another tissue property from the region of interest. The proton density map having a total signal intensity that includes a proton density signal and a receiver sensitivity profile signal. The method also includes quantifying the proton density signal and the receiver sensitivity profile signal using parameters provided by the proton density map and the tissue property map, and generating a quantitative map from the region of interest based on the proton density signal.

In another aspect of the disclosure, a system is provided that includes a magnet system configured to generate a polarizing magnetic field about at least a portion of a subject. The system also includes a magnetic gradient system including a plurality of magnetic gradient coils configured to apply at least one magnetic gradient field to the polarizing magnetic field and a radio frequency (RF) system configured to apply an RF field to the subject and to receive magnetic resonance signals from the subject using a coil array. The system further includes a computer system programmed to control the magnetic gradient system and the RF system to acquire MRF data from a region of interest in a subject by performing a pulse sequence using a series of varied sequence blocks to elicit a series of signal evolutions. The computer system is also configured to compare the MRF data to a MRF dictionary to simultaneously map proton density and a tissue property from the region of interest, the proton density map having a proton density signal and a receiver sensitivity profile signal and determine the proton density signal and the receiver sensitivity profile signal based at least on values provided by the proton density map and the tissue property map. The computer system is also configured to generate a quantitative map from the region of interest based on the proton density signal.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
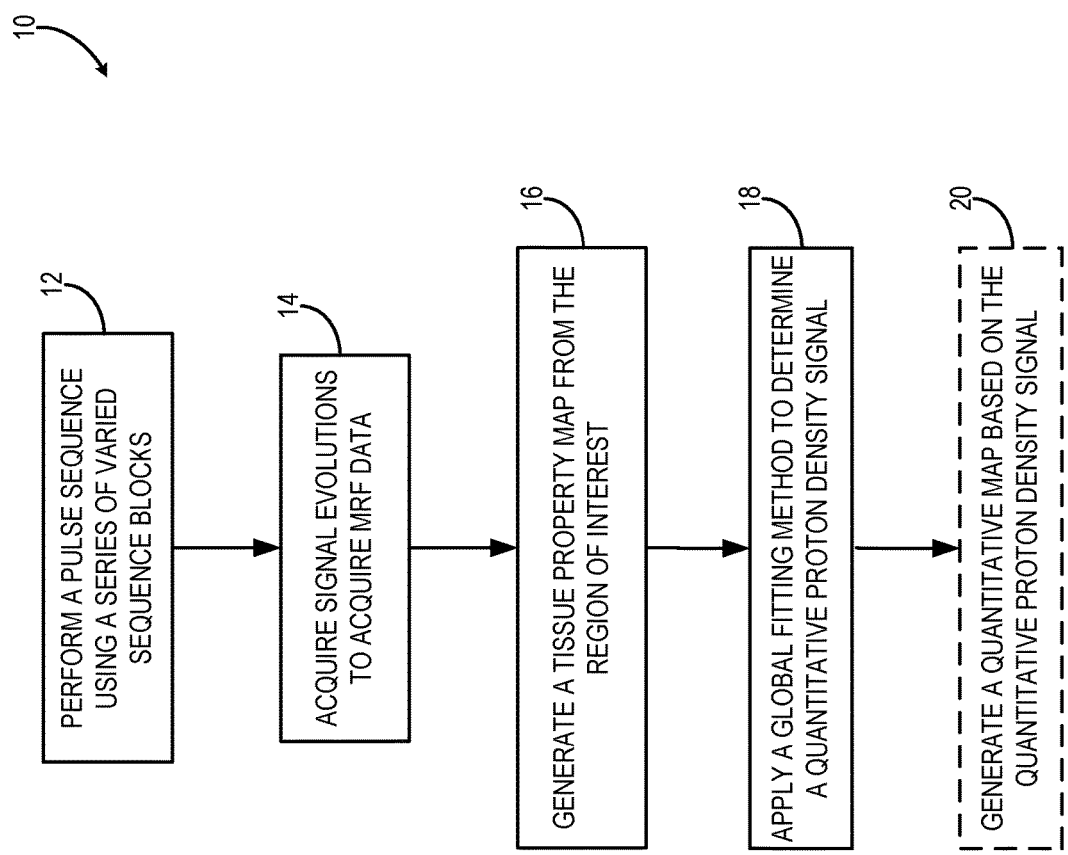
FIG. 1 is a schematic flow chart illustrating one non-limiting example of a process in accordance with the present disclosure.

Magnetic resonance fingerprinting ("MRF") is a technique that facilitates mapping of tissue or other material properties based on random or pseudorandom or otherwise varied measurements of the subject or object being imaged. In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The random or pseudorandom or otherwise varied measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE"), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom or otherwise varied, and may contain signals from different materials or tissues that are spatially incoherent, temporally incoherent, or both, MRF processes can be designed to map any of a wide variety of parameters. These parameters may be mapped individually or simultaneously. Examples of such parameters that can be mapped may include, but are not limited to, longitudinal relaxation time ($T_1$), transverse relaxation time ($T_2$), main or static magnetic field map ($B_0$), and proton density (PD). MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. The dictionary may also comprise a series of previously acquired known evolutions. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha, \phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation differences; and $M_0$ is the magnetization in the default or natural alignment to which spins align when placed in the main magnetic field.

While $E_i(T_1,T_2, D)$ is provided as an example, in different situations, the decay term, $E_i(T_1,T_2, D)$, may also include additional terms, $E_i(T_1,T_2, D ...)$ or may include fewer terms, such as by not including the diffusion relaxation, as $E_i(T_1,T_2)$ or $E_i(T_1,T_2, ...)$. Also, the summation on "j" could be replace by a product on "j".

The dictionary may store signals described by, $$S_i = R_i E_i(S_{i-1}) \quad (2);$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

As described, MRF provides a framework for multiple tissue parameter mapping based on a single acquisition. This framework combines the transient state of the signal evolution with dictionary matching to generate multi-parameter maps. Unlike conventional MR systems, tissue property maps may be generated simultaneously using MRF. Thus, rather than subjecting a patient to multiple serial acquisitions that may take a half hour or more, the patient may experience a much shorter time in the bore. Similarly, rather than making a radiologist wait for multiple images that are produced serially (e.g., a first pulse sequence to generate a $T_1$ map, a second pulse sequence to generate a $T_2$ map), the radiologist may be provided with maps that are produced simultaneously from the MRF data.

Conventional MRF systems may be used to simultaneously map proton density and compute estimates of tissue fractions. Typically, proton density maps are generated by measuring all parameters that influence the total signal intensity, followed by subsequent weighting of the image. However, proton density mapping can be subject to image intensity bias that may impair the accuracy of the measured results, making quantitative proton density mapping a challenging task. In particular, non-uniformities imposed by spatial variations of the receiver coil sensitivity profile add concomitant signal intensity to proton density mapping. The concomitant receiver sensitivity profile signal precludes quantitative proton mapping unless it is removed.

Thus, as will be described, the present disclosure presents an approach for MRF that corrects for receiver sensitivity bias and allows for quantitative proton density mapping. The present disclosure further presents a method for using the quantitative proton density maps to generate absolute tissue fraction maps from the region of interest.

Referring to FIG. 1 a flowchart is provided for one implementation of a method 10 for quantitative proton density mapping in accordance with the present disclosure. To start, the method 10 includes performing a pulse sequence using a series of varied sequence blocks 12, such as described above, to elicit a series of signal evolutions and acquire MRF data 14. Some examples of MRF pulse sequences include, for example, fast imaging with steady state free-precession (FISP) or balanced steady state free-precession (bSSFP) that are modified to include the above-described varied sequence blocks to elicit the signal evolutions.

The varied sequence blocks may vary in a number of parameters to generate different signal evolutions for different tissues from the region of interest. The varied sequence blocks may vary parameters including, but not limited to, echo time, flip angle, phase encoding, RF pulse amplitude, RF pulse phase, number of RF pulses, and type of gradient applied, as described above. Acquiring the MRF data 14 may include sampling k-space using a spiral trajectory. In one non-limiting example, a variable-density spiral trajectory using a minimum-time gradient design with zero moment compensation is used to acquire data.

The method 10 further includes comparing the MRF data to a MRF dictionary 14 to map at least one tissue property from the region of interest. As described, the dictionary may be generated in a number of ways, for example, by comparing the data to known evolutions or using Bloch simulations. In one non-limiting example, the dictionary may be generated using an extended phase graph (EPG) formalism algorithm. EPG provides a powerful tool to predict the timing and the amplitude of echo formation. In the EPG algorithm, any pulse sequence can be represented by effects of RF pulses, $T_1$ and $T_2$ relaxation, and dephasing due to unbalanced gradient moments. The spin system, affected by the pulse sequence, is described as a discrete set of phase states, which makes it an efficient way to simulate the signal evolution with unbalanced gradients, such as with FISP.

Comparing the MRF data to the MRF dictionary 14 may further include applying a pattern recognition method to match the signal evolutions to a dictionary entry. In one non-limiting example, the inner products between the normalized measured time course of each pixel and all entries of the normalized dictionary were calculated, and the dictionary entry corresponding to the maximum value of the inner product was taken to represent the closest signal evolution to the one acquired.

The method 10 further includes generating a tissue property map 16 from the region of interest. Some tissue property maps may include, for example, relaxation parameters, tissue fractions, and proton density maps. As described above, given the non-uniformities imposed by spatial variations, MRF derived proton density maps include signals attributed to both a receiver sensitivity profile and a proton density. The proton density map may be expressed by:

$$M_0 = (PD)(RP) \quad (3);$$

where $M_0$ is the proton density map, PD is the proton density signal, and RP is the receiver profile signal. Measuring RP is challenging, especially at high field strengths. To overcome this issue, the present disclosure proposes using a fitting method 18 to correct receiver bias and determine a quantitative proton density signal from the region of interest. The fitting may be a global fitting. The quantitative proton density signal is then used to generate a quantitative map 20 from the region of interest.

In one aspect, the fitting method 18 includes generating a proton density map and another tissue property map from the region of interest. In one non-limiting example of an implementation, because the receiver sensitivity profile signal does not affect quantitative MRF $T_1$ maps, the present disclosure may use a $T_1$ map from the region of interest to form an estimated proton density signal, which may then be used to form an estimate of the receiver sensitivity profile signal. One non-limiting example for relationship may be approximated using Eqn. 2:

$$\frac{1}{PD} \approx A + \left(\frac{1}{T_1}\right)B; \quad (4);$$

where A and B are constants. The proton density map may be normalized to a tissue in the region of interest, for example, white matter, gray matter, and cerebrospinal fluid. In one non-limiting example, a pure cerebrospinal fluid voxel may be chosen as an internal proton density reference and the proton density map may be normalized to the pure cerebrospinal fluid signal. An alternative reference (within the brain or outside of the brain) or external proton density reference substance can also be used.

The fitting method 18 further includes estimating the proton density signal by providing an initial value for the A and B constants, and taking $T_1$ values from the region of interest. In one non-limiting example, $T_1$ values are taken from gray matter and white matter. The estimated receiver sensitivity profile signal is estimated using the estimated proton density signal and the normalized proton density map, following application of a smoothing filter, such as a Gaussian filter. The estimated receiver sensitivity profile signal is then fit to a polynomial and extrapolated across the region of interest. In one non-limiting example, the polynomial may comprise a 2nd order 2D polynomial.

The fitted receiver profile signal is then used to determine a fitted proton density signal across the region of interest. The fitted proton density signal is normalized to a tissue in the region of interest, and then used to recalculate the A and B constants. The fitting method 18 is repeated until the A and B constants reach a steady-state value. Thus, an iterative process may be used to determine A and B constraints. The steady-state value may be defined as being approximately constant within a specified tolerance. In one aspect, the specified tolerance may be defined such that the A and B constants change by less than 20%, or less than 15%, or less than 10%, or less than 5%, or less than 1%, or less than 0.1% between iterations.

Once the A and B constants reach the steady-state value, a quantitative proton density signal is determined. The quantitative proton density signal may be used to generate a quantitative map 20 from the region of interest. Suitable quantitative maps 20 may include absolute tissue fraction maps. The absolute tissue fraction maps may be generated by voxelwise multiplication of a relative tissue fraction map and the quantitative proton density signal. That is, specific tissues within the region of interest may be attributed to voxel magnetization, thus providing absolute tissue fraction mapping from the region of interest.

Figure 2:
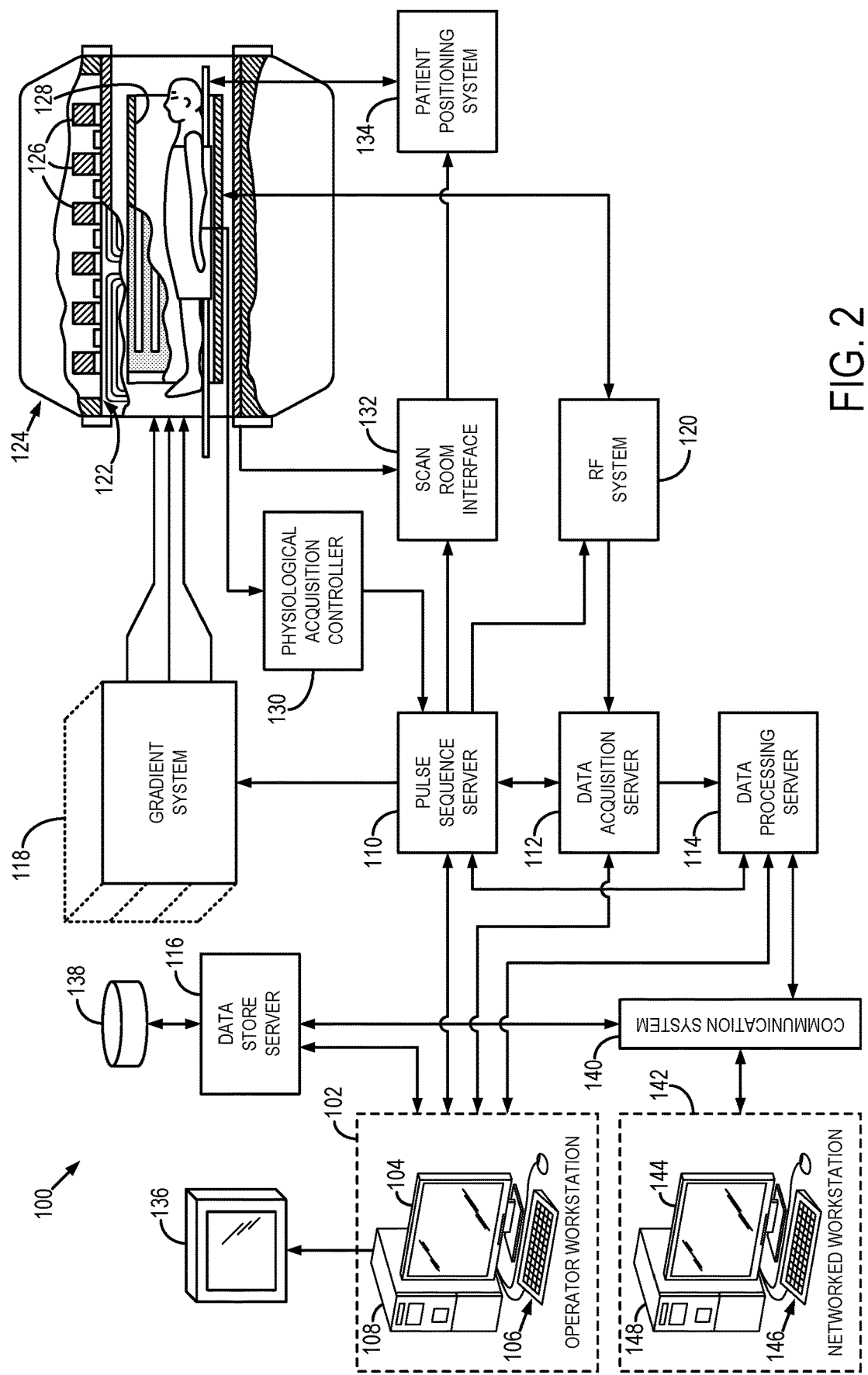
FIG. 2 is a block diagram of an example magnetic resonance fingerprinting ("MRF") system that can be used to implement the methods described in the present disclosure.

Referring particularly now to FIG. 2, an example of an MRF system 100 that can implement the methods described here is illustrated. The MRF system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRF system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRF pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{5};$$

and the phase of the received magnetic resonance signal may also be determined according to the following relationship:

$$\varphi = \tan^{-1}\left(\frac{Q}{I}\right). \tag{6}$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRF system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

EXAMPLES

The following examples set forth, in detail, ways in which the spectroscopic magnetic resonance fingerprinting system 100 may be used or implemented, and will enable one of skill in the art to more readily understand the principles thereof. The following examples are presented by way of illustration and are not meant to be limiting in any way.

Volunteers were scanned with FISP-MRF at 3T (Skyra, Siemens Healthcare, Erlangen, Germany). To evaluate the technique for different receiver profiles, the same acquisition was performed with a 20-channel head coil and the body coil. MRF parameters were as follows: $TR_{min}$: 8.64 ms, maximum flip angle 30°, 3000 frames, FOV 300 mm, resolution 1.17×1.17×5 mm. Voxelwise dictionary matching was based on the inner product.

T1 and T2 values corresponding to pure GM, WM, and CSF, and partial volumes were identified by 7-component k-means analysis. Clusters identifying pure WM, pure GM, and WM/GM partial volumes were included in a mask for PD fitting. MRF tissue fraction maps for WM, GM, and CSF were estimated using a dictionary-based approach.

The fitting method 18 was applied, and absolute tissue maps were created by voxelwise multiplication of the tissue fractions with the normalized PD. ROIs 7 mm×7 mm were placed bilaterally in various brain structures for quantitative comparisons.

Figure 3:
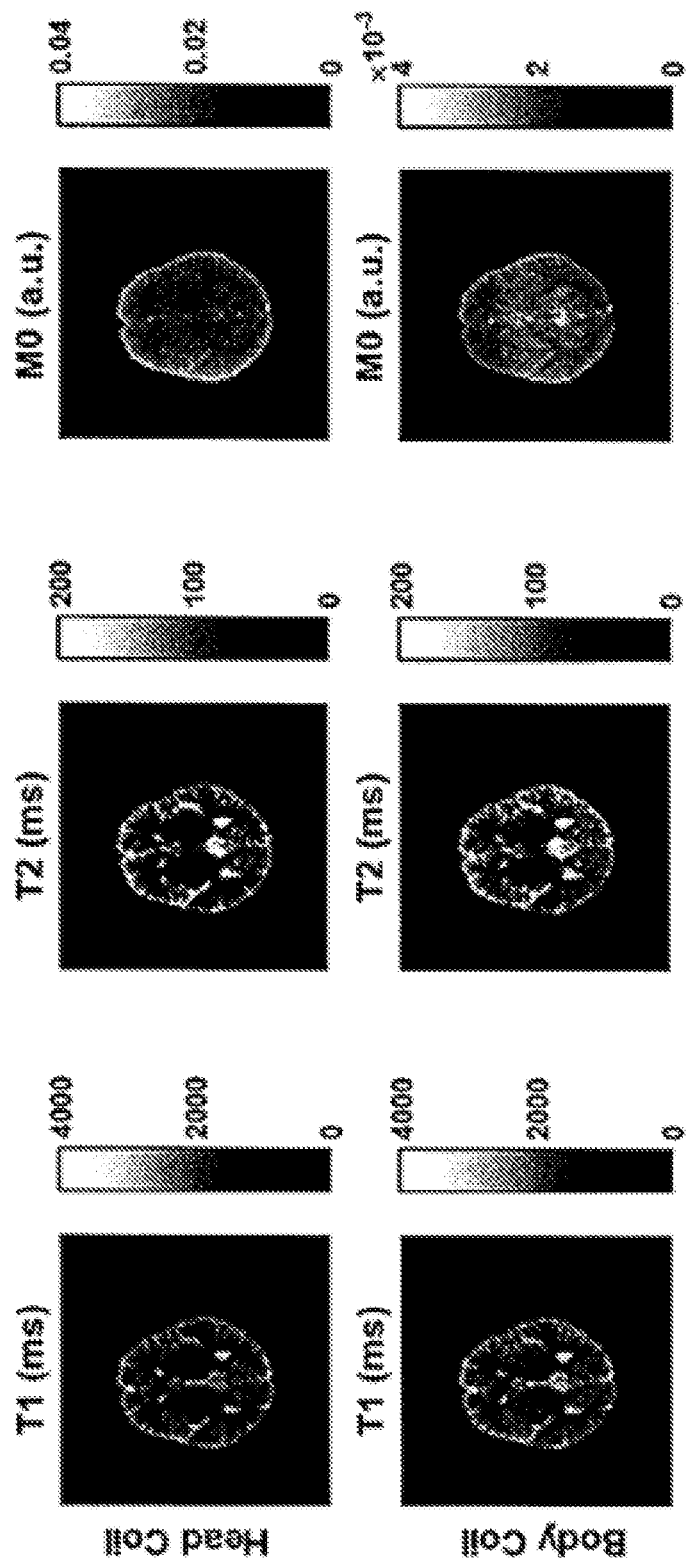
FIG. 3 is a map of proton density using a head and body coil, the proton density map illustrates the effect of different receiver profiles.

FIG. 3 shows MRF relaxation and proton density maps measured from head and body coils. The MRF proton density maps illustrate the effect of different receiver sensitivity profiles.

Figure 4:
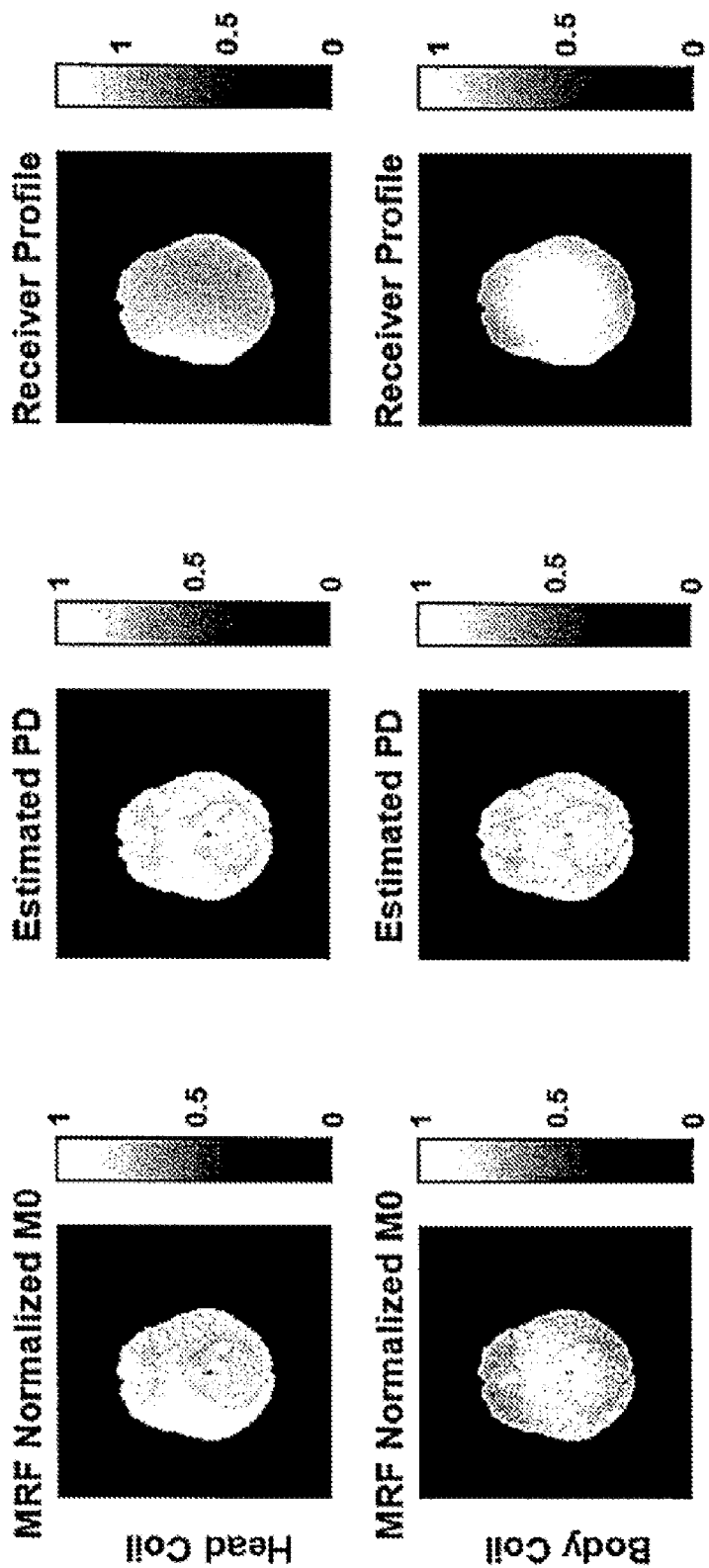
FIG. 4 is a normalized proton density map, a proton density signal map, and a receiver sensitivity profile signal map.

FIG. 4 shows a normalized proton density map, and estimated proton density signals and receiver sensitivity profile signals after 7 iterations. The mean proton density PD values are in very close agreement across structures (see Table 1 below). Fitted constants for Eqn 2 were $A_{HC}$=0.788, $B_{HC}$=395 ms in the head coil, and $A_{BC}$=0.824, $B_{BC}$=352 ms in the body coil.

Figure 5:
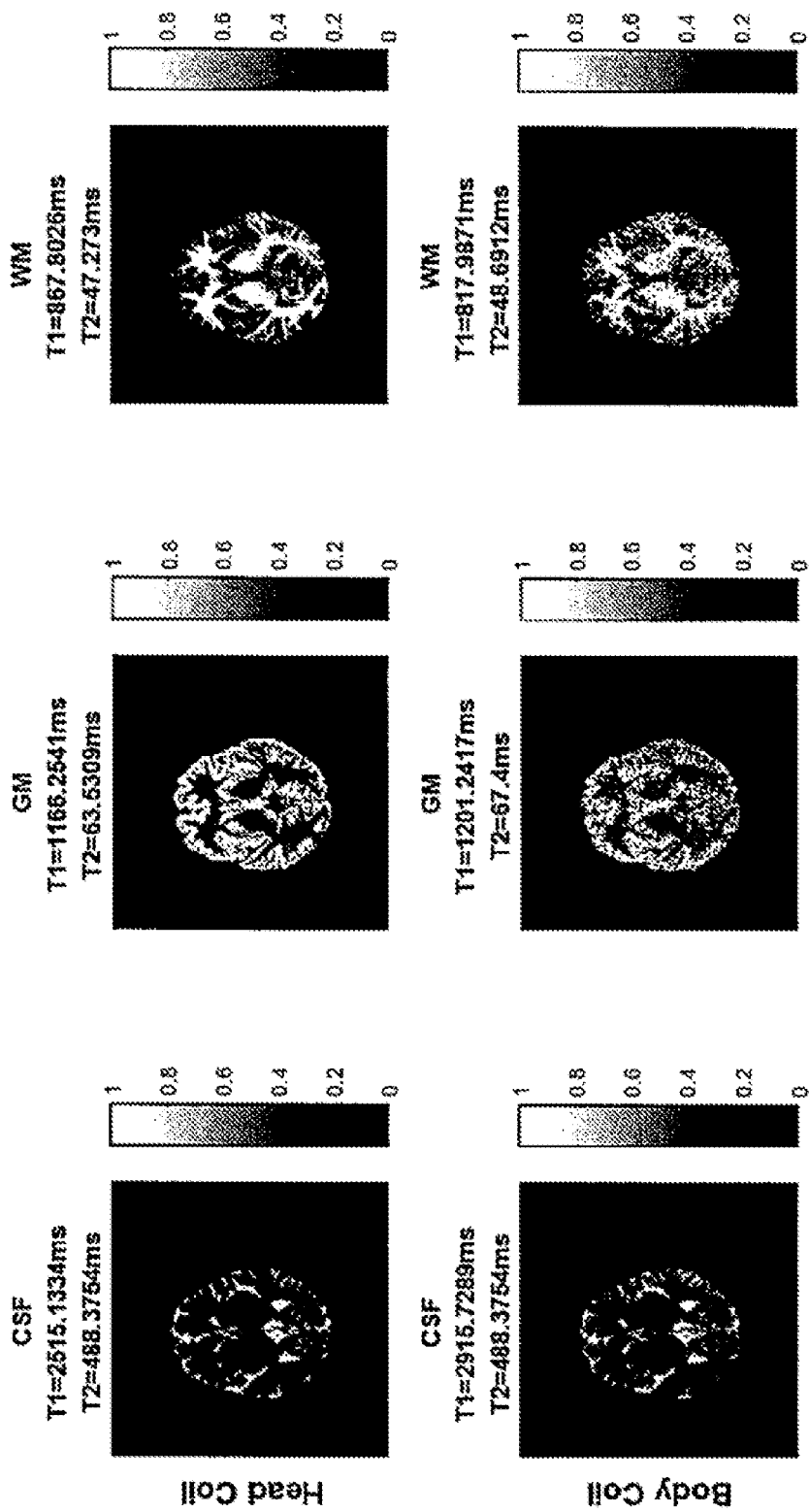
FIG. 5 is a relative tissue fraction map for cerebrospinal fluid, gray matter, and white matter.

FIG. 5 shows tissue fraction maps for CSF, GM, and WM. T1 and T2 values of each tissue type in the PV analysis differ by 5% or less between the two acquisitions, even given the noisy body coil results.

Figure 6:
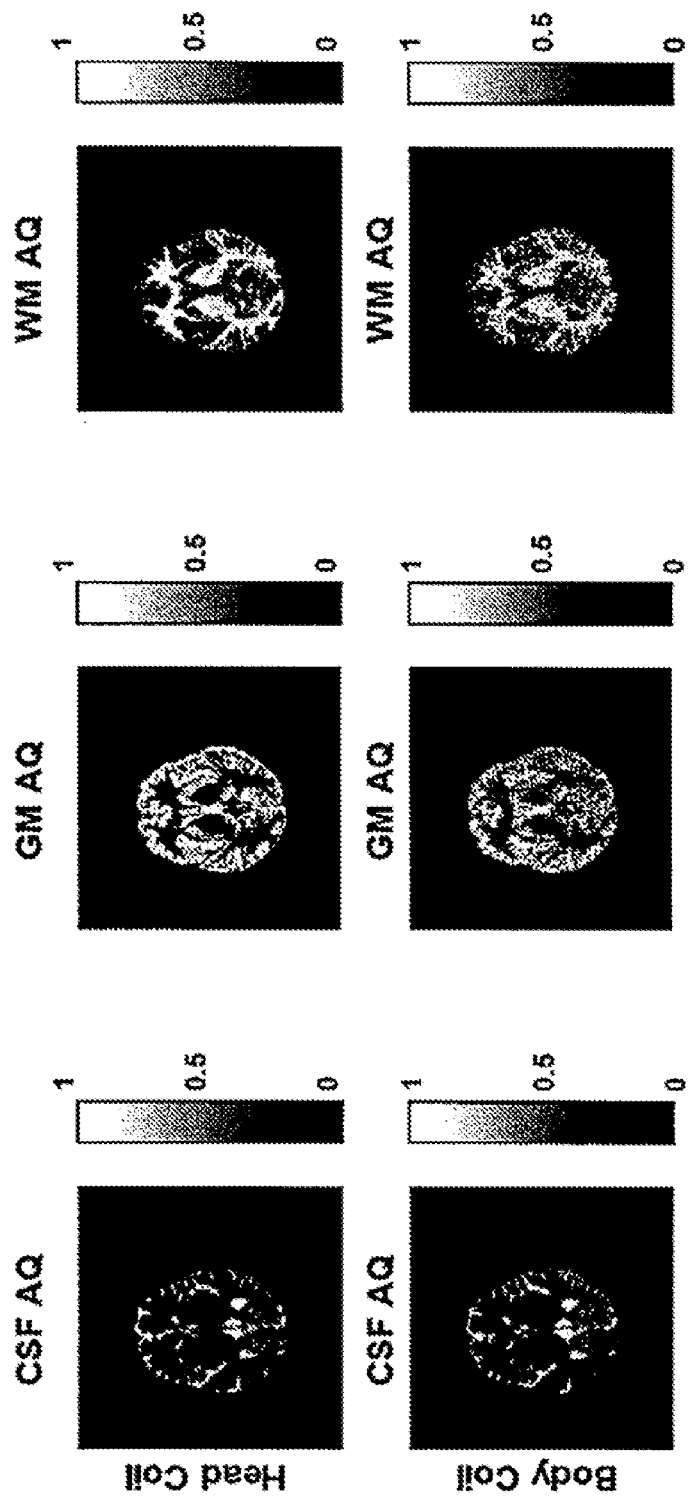
FIG. 6 is an absolute tissue fraction map for cerebrospinal fluid, gray matter, and white matter.

FIG. 6 shows absolute quantity maps for CSF, GM, and WM as a fraction of the equilibrium magnetization. Absolute quantities in each ROI are shown in Table 1.

TABLE 1

Quantified relaxation parameters, proton density (PD), and absolute tissue quantities (AQ) in various brain structures. HC values are measured with a 20-channel head coil, BC values are measured with the body coil. Values are reported as mean (standard deviation).

| Structure | T1 (ms) HC | T1 (ms) BC | T2 (ms) HC | T2 (ms) BC | PD HC | PD BC | CSF AQ HC | CSF AQ BC |
|---|---|---|---|---|---|---|---|---|
| Frontal WM | 807 (25) | 779 (129) | 49 (4) | 52 (10) | 0.78 (0.01) | 0.76 (0.05) | 0 (0.01) | 0.01 (0.03) |
| Putamen | 1151 (46) | 1096 (132) | 53 (3) | 54 (8) | 0.89 (0.02) | 0.90 (0.04) | 0 (0) | 0.01 (0.03) |
| Pallidum | 921 (40) | 873 (101) | 34 (2) | 34 (6) | 0.86 (0.02) | 0.88 (0.05) | 0 (0) | 0 (0) |
| Thalamus | 1107 (80) | 1031 (134) | 51 (4) | 56 (11) | 0.86 (0.03) | 0.87 (0.05) | 0 (0) | 0.03 (0.06) |
| Parietal WM | 861 (74) | 826 (137) | 49 (7) | 54 (15) | 0.79 (0.03) | 0.79 (0.05) | 0 (0.01) | 0.03 (0.05) |
| Ventricle | 2284 (463) | 2747 (679) | 455 (220) | 461 (199) | 0.92 (0.06) | 0.94 (0.08) | 0.74 (0.20) | 0.80 (0.22) |

| GM AQ | WM AQ |

TABLE 1-continued

Quantified relaxation parameters, proton density (PD), and absolute tissue quantities (AQ) in various brain structures. HC values are measured with a 20-channel head coil, BC values are measured with the body coil. Values are reported as mean (standard deviation).

| Structure | HC | BC | HC | BC |
| --- | --- | --- | --- | --- |
| Frontal WM | 0 (0) | 0.06 (0.11) | 0.77 (0.02) | 0.69 (0.10) |
| Putamen | 0.67 (0.11) | 0.53 (0.25) | 0.22 (0.11) | 0.36 (0.23) |
| Pallidum | 0 (0.04) | 0.03 (0.10) | 0.86 (0.04) | 0.85 (0.10) |
| Thalamus | 0.47 (0.22) | 0.36 (0.30) | 0.39 (0.20) | 0.47 (0.25) |
| Parietal WM | 0.10 (0.17) | 0.07 (0.13) | 0.69 (0.14) | 0.69 (0.12) |
| Ventricle | 0 (0) | 0.01 (0.04) | 0.17 (0.14) | 0.14 (0.15) |

The present disclosure demonstrates the ability to estimate PD and receiver profile directly from MRF, which can also be used to generate quantitative maps of T1, T2, and tissue fractions. Estimated PD maps are in good agreement in multiple acquisitions, demonstrating robust separation of different receiver profile effects. This approach could have implications beyond MRF, potentially providing high quality B1-maps at high field strengths. The present disclosure combines the PD and tissue fraction maps to quantify the relative contribution of each tissue type to the voxel magnetization. The PD and RP estimation presented here uses a fitting approach. Accurate PD and RP estimates may also be obtained through multi-channel fitting. B1+ mapping may further improve the accuracy of these maps.

The present disclosure has described one or more preferred embodiments, and it should be appreciated that many equivalents, alternatives, variations, and modifications, aside from those expressly stated, are possible and within the scope of the invention.

The invention claimed is:

1. A method for correcting receiver bias during quantitative proton density mapping with magnetic resonance fingerprinting (MRF), the method comprising:
    acquiring MRF data from a region of interest in a subject by performing a pulse sequence using a series of varied sequence blocks to elicit a series of signal evolutions;
    comparing the MRF data to a MRF dictionary to generate a proton density map and another tissue property map from the region of interest, the proton density map having a proton density signal and a receiver sensitivity profile signal;
    generating an estimated proton density signal using parameters from the tissue property map;
    generating an estimated receiver sensitivity profile signal using the estimated proton density signal;
    generating a fitted receiver profile signal using the estimated receiver sensitivity profile signal, and a fitted proton density signal using the fitted receiver profile signal; and
    generating a quantitative map from the region of interest based at least in part on the fitted proton density signal and the fitted receiver profile signal.

2. The method of claim 1 wherein the tissue property map comprises a relaxation parameter.

3. The method of claim 2 wherein the relaxation parameter includes $T_1$.

4. The method of claim 1, wherein the quantitative map comprises an absolute tissue fraction from the region of interest.

5. A method for correcting receiver bias during quantitative proton density mapping with magnetic resonance fingerprinting (MRF), the method comprising:
    acquiring MRF data from a region of interest in a subject by performing a pulse sequence using a series of varied sequence blocks to elicit a series of signal evolutions;
    comparing the MRF data to a MRF dictionary to map proton density and another tissue property from the region of interest, the proton density map having a proton density signal and a receiver sensitivity profile signal;
    quantifying the proton density signal and the receiver sensitivity profile signal using parameters provided by the proton density map and the tissue property map; and
    generating a quantitative map from the region of interest based on the proton density signal,
    wherein the quantitative map comprises an absolute tissue fraction from the region of interest.

6. The method of claim 5 wherein the absolute tissue fraction is determined from a voxelwise multiplication of the proton density signal and a relative tissue fraction map.

7. The method of claim 6 wherein comparing the MRF data to the MRF dictionary further comprises simultaneously mapping the relative tissue fraction map from the region of interest.

8. A method for correcting receiver bias during quantitative proton density mapping with magnetic resonance fingerprinting (MRF), the method comprising:
    acquiring MRF data from a region of interest in a subject by performing a pulse sequence using a series of varied sequence blocks to elicit a series of signal evolutions;
    comparing the MRF data to a MRF dictionary to map proton density and another tissue property from the region of interest, the proton density map having a proton density signal and a receiver sensitivity profile signal;
    quantifying the proton density signal and the receiver sensitivity profile signal using parameters provided by the proton density map and the tissue property map; and
    generating a quantitative map from the region of interest based on the proton density signal,
    wherein determining the proton density signal and the receiver sensitivity profile signal includes using a fitting method, the fitting method comprising a set of expressions described at least by:

$$M_0 = (PD)(RP);$$

$$\frac{1}{PD} \approx A + \left(\frac{1}{T_1}\right)B;$$

and
where:

M₀ is the proton density map;
PD is the proton density signal;
RP is the receiver profile signal; and
A and B are constants.

9. The method of claim 8 wherein determining the proton density signal and the receiver sensitivity profile signal includes normalizing the proton density map to a material in the region of interest.

10. The method of claim 9 wherein the material is selected from within the brain and includes white matter, gray matter, or cerebrospinal fluid, or is selected from outside the brain includes a desired tissue.

11. The method of claim 8 wherein the fitting method includes providing an initial value for the A and B constants to solve for an estimated proton density signal and an estimated receiver sensitivity profile signal.

12. The method of claim 11 wherein the fitting method further includes applying a smoothing filter prior to solving for the estimated receiver sensitivity profile signal.

13. The method of claim 12 wherein the estimated receiver sensitivity profile signal is fit to a polynomial and extrapolated across the region of interest to solve for a fitted proton density signal.

14. The method of claim 13 wherein the A and B constants are recalculated using the fitted proton density signal, and the fitting method is repeated until the A and B constants reach a steady-state value, the steady-state value being approximately constant within a specified tolerance.

15. A system comprising:
   a magnet system configured to generate a polarizing magnetic field about at least a portion of a subject;
   a magnetic gradient system including a plurality of magnetic gradient coils configured to apply at least one magnetic gradient field to the polarizing magnetic field;
   a radio frequency (RF) system configured to apply an RF field to the subject and to receive magnetic resonance signals from the subject using a coil array;
   a computer system programmed to:
      control the magnetic gradient system and the RF system to acquire MRF data from a region of interest in a subject by performing a pulse sequence using a series of varied sequence blocks to elicit a series of signal evolutions;
      compare the MRF data to a MRF dictionary to generate a proton density map and a tissue property map from the region of interest, the proton density map having a proton density signal and a receiver sensitivity profile signal;
      generate an estimated proton density signal using parameters from the tissue property map;
      generate an estimated receiver sensitivity profile signal using the estimated proton density signal;
      generate a fitted receiver profile signal using the estimated receiver sensitivity profile signal, and a fitted proton density signal using the fitted receiver profile signal; and
      generate a quantitative map from the region of interest based at least in part on the fitted proton density signal and the fitted receiver profile signal.

16. The system of claim 15 wherein the quantitative comprises an absolute tissue fraction from the region of interest.

* * * * *